(12) United States Patent
Gupta

(10) Patent No.: US 11,929,179 B2
(45) Date of Patent: Mar. 12, 2024

(54) MULTI-MODAL MACHINE LEARNING MEDICAL ASSESSMENT

(71) Applicant: Danika Gupta, Saratoga, CA (US)

(72) Inventor: Danika Gupta, Saratoga, CA (US)

( * ) Notice: Subject to any disclaimer, the term of this patent is extended or adjusted under 35 U.S.C. 154(b) by 0 days.

(21) Appl. No.: 18/185,479

(22) Filed: Mar. 17, 2023

(65) Prior Publication Data

US 2023/0420128 A1 Dec. 28, 2023

Related U.S. Application Data

(63) Continuation of application No. 17/849,700, filed on Jun. 26, 2022.

(51) Int. Cl.
| | |
|---|---|
| *G06N 20/00* | (2019.01) |
| *G06N 3/08* | (2023.01) |
| *G06N 20/20* | (2019.01) |
| *G16H 50/20* | (2018.01) |
| *G16H 50/30* | (2018.01) |

(52) U.S. Cl.
CPC .............. *G16H 50/20* (2018.01); *G06N 3/08* (2013.01); *G06N 20/00* (2019.01); *G06N 20/20* (2019.01); *G16H 50/30* (2018.01)

(58) Field of Classification Search
None
See application file for complete search history.

(56) References Cited

U.S. PATENT DOCUMENTS

| | | | |
|---|---|---|---|
| 11,263,749 B1 * | 3/2022 | Purushottam | G16H 10/60 |
| 2021/0296002 A1 * | 9/2021 | Jia | G16H 50/70 |
| 2022/0378361 A1 * | 12/2022 | Lee | A61B 5/7275 |
| 2023/0011166 A1 * | 1/2023 | Solomon | G16H 50/20 |
| 2023/0028983 A1 * | 1/2023 | Oechsle | G06F 16/904 |

FOREIGN PATENT DOCUMENTS

WO WO-2021188825 A1 * 9/2021 ............ C12Q 1/6883

\* cited by examiner

*Primary Examiner* — David R Vincent
(74) *Attorney, Agent, or Firm* — Kunzler Bean & Adamson

(57) ABSTRACT

Apparatuses, systems, methods, and computer program products are disclosed for multi-modal machine learning medical assessment. A source module is configured to receive multiple types of data for a user. A machine learning module is configured to analyze the multiple types of data using machine learning to determine multiple predictions of likelihoods of the user getting a neurological disease. A multi-modal result module configured to determine a single result indicating a likelihood of the user getting the neurological disease based on the multiple predictions.

20 Claims, 5 Drawing Sheets

MULTI-MODAL MACHINE LEARNING MEDICAL ASSESSMENT

CROSS-REFERENCES TO RELATED APPLICATIONS

This is a continuation application of and claims priority to U.S. patent application Ser. No. 17/849,700 entitled "MULTI-MODAL MACHINE LEARNING MEDICAL ASSESSMENT" and filed on Jun. 26, 2022, which is incorporated herein by reference.

FIELD

This invention relates to medical assessments and more particularly relates to a multi-modal machine learning medical assessment.

BACKGROUND

Early detection of neurological illnesses such as Alzheimer's can be difficult. However, when detected early, progress of a neurological illness can often be treated and/or slowed.

SUMMARY

Apparatuses are presented for multi-modal machine learning medical assessment. In one embodiment, a source module is configured to receive multiple types of data for a user. A machine learning module, in certain embodiments, is configured to analyze the multiple types of data using machine learning to determine multiple predictions of likelihoods of the user getting a neurological disease. In a further embodiment, a multi-modal result module is configured to determine a single result indicating a likelihood of the user getting the neurological disease based on the multiple predictions.

An apparatus, in another embodiment, includes means for receiving multiple types of data for a user. In some embodiments, an apparatus includes means for analyzing the multiple types of data using machine learning to determine multiple predictions of likelihoods of the user getting a neurological disease. An apparatus, in certain embodiments, includes means for determining a single result indicating a likelihood of the user getting the neurological disease based on the multiple predictions.

Methods are presented for multi-modal machine learning medical assessment. In one embodiment, a method includes receiving multiple types of data for a user. In a further embodiment, a method includes analyzing the multiple types of data using machine learning to determine multiple predictions of likelihoods of the user getting a neurological disease. A method, in some embodiments, includes determining a single result indicating a likelihood of the user getting the neurological disease based on the multiple predictions.

Computer program products comprising a computer readable storage medium are presented. In certain embodiments, a computer readable storage medium stores computer usable program code executable to perform operations for multi-modal machine learning medical assessment. In some embodiments, one or more of the operations may be substantially similar to one or more steps described above with regard to the disclosed apparatuses, systems, and/or methods.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Figure 1:
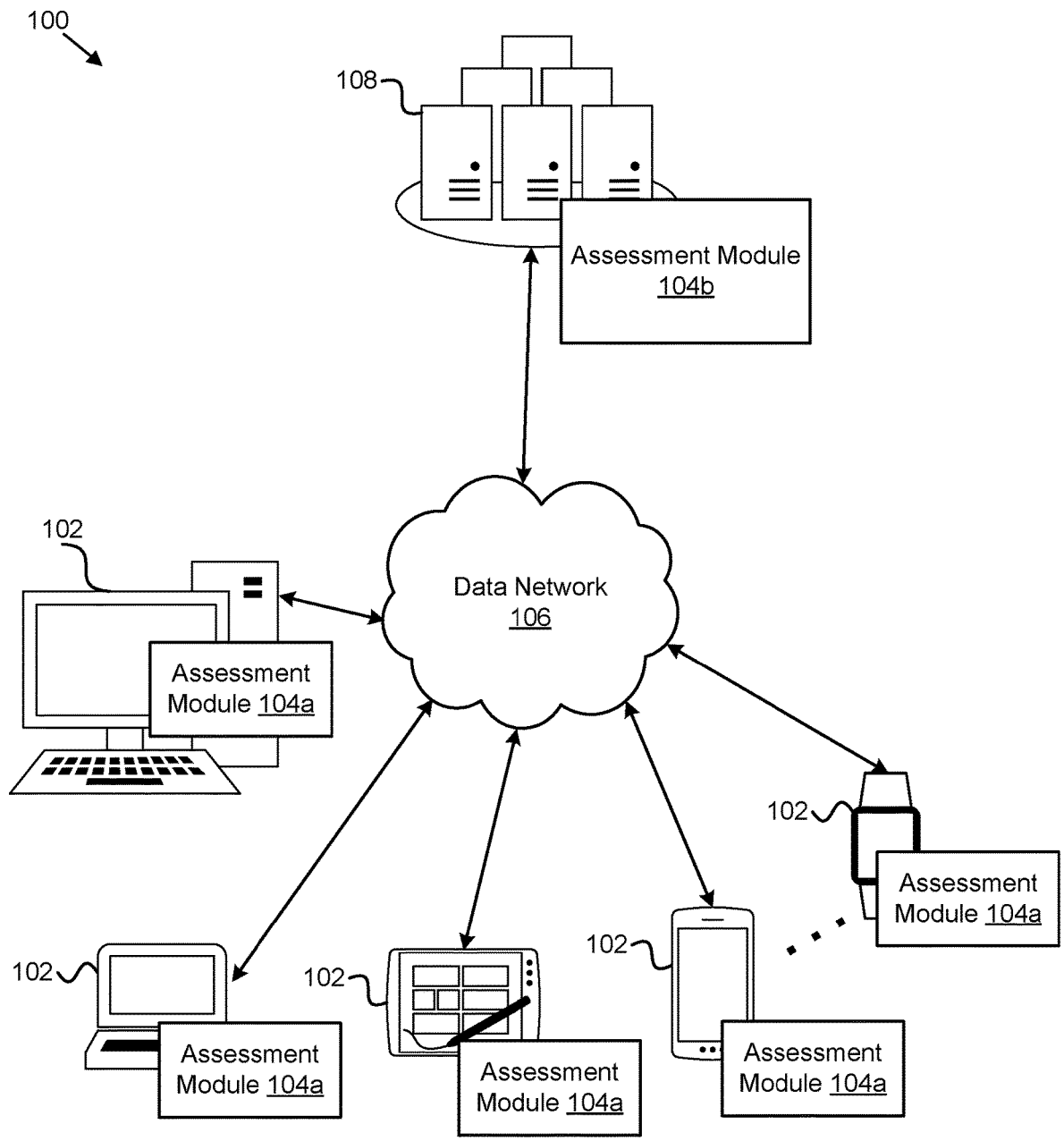
FIG. 1 is a schematic block diagram illustrating one embodiment of a system for multi-modal machine learning medical assessment.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

These features and advantages of the embodiments will become more fully apparent from the following description and appended claims, or may be learned by the practice of embodiments as set forth hereinafter. As will be appreciated by one skilled in the art, aspects of the present invention may be embodied as a system, method, and/or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present invention may take the form of a computer program product embodied in one or more computer readable medium(s) having program code embodied thereon.

Many of the functional units described in this specification have been labeled as modules (or components), in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of program code may be a single instruction, or many instructions, and may even be distributed over several different code segments, among different programs, and across several memory devices Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the program code may be stored and/or propagated on in one or more computer readable medium(s).

The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory ("RAM"), a read-only memory ("ROM"), an erasable programmable read-only memory ("EPROM" or Flash memory), a static random access memory ("SRAM"), a portable compact disc read-only memory ("CD-ROM"), a digital versatile disk ("DVD"), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The schematic flowchart diagrams and/or schematic block diagrams in the Figures illustrate the architecture, functionality, and operation of possible embodiments of apparatuses, systems, methods and computer program products according to various embodiments of the present invention. In this regard, each block in the schematic flowchart diagrams and/or schematic block diagrams may represent a module, segment, or portion of code, which comprises one or more executable instructions of the program code for implementing the specified logical function(s).

It should also be noted that, in some alternative embodiments, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

FIG. 1 depicts one embodiment of a system 100 for multi-modal machine learning medical assessment. In one embodiment, the system 100 includes one or more hardware computing devices 102, one or more assessment modules 104 (e.g., one or more assessment modules 104a disposed on the one or more hardware computing devices 102, one or more backend assessment modules 104b, or the like), one or more data networks 106 or other communication channels, and/or one or more backend server devices 108. In certain embodiments, even though a specific number of hardware computing devices 102, assessment modules 104, data networks 106, and/or backend server devices 108 are depicted in FIG. 1, one of skill in the art will recognize, in light of this disclosure, that any number of hardware computing devices 102, assessment modules 104, data networks 106, and/or backend server devices 108 may be included in the system 100 for multi-modal machine learning medical assessment.

In general, an assessment module 104, in various embodiments, is configured to receive and/or collect multiple types of data (e.g., image data, volumetric data, evaluation data, or the like) for a user (e.g., a patient, another user, or the like) and/or to assess and/or diagnose the presence and/or severity of one or more neurological diseases (e.g., Alzheimer's disease, Parkinson's disease, Multiple Sclerosis, Amyotrophic Lateral Sclerosis (ALS), or the like) based on machine learning analyses for the multiple types of data. An assessment module 104 may receive data from a user, from a medical professional evaluating a user, from a computing device 102, from a backend server device 108, over a data network 106, from one or more user interface elements of a hardware computing device 102 and/or a backend server device 108, or the like. An assessment module 104 may provide a single, combined result (e.g., an assessment, or the like) to a user (e.g., a patient, a medical professional, or the like).

Based on a machine learning analysis of the multiple types of data, an assessment module 104 may assess and/or diagnose a likelihood of a user getting one or more neurological diseases or other medical conditions. For example, after an assessment module 104 receives multiple types of data for a user, an assessment module 104 may analyze and/or score the different types of data using machine learning to determine multiple predictions of likelihoods of the user getting a neurological disease, determine a single result indicating a likelihood of the user getting a neurological disease based on the multiple predictions, and/or may provide the single result to a user (e.g., the user being evaluated, a medical professional, or the like) in a user interface of an electronic display screen of a hardware computing device 102, through an application programming interface (API), or the like. An assessment module 104 may analyze the multiple types of data using one or more machine learning models trained for a certain neurological disease and/or other medical condition.

An assessment module 104 may compare a user's data to previous data from when the user was healthy (e.g., to baseline data). An assessment module 104 may normalize results based on a user's demographic (e.g., age, gender, or the like). An assessment module 104 may determine normalization data as part of training process, determining a range of expected scores for each demographic, or the like.

In certain embodiments, an assessment module 104 determining whether or not a user is likely to get a neurological disease may facilitate early detection of the neurological disease, allowing more effective treatment of the neurological disease, better quality of life for the user, or the like. An assessment module 104 using multiple modalities, or types of data, in some embodiments, may provide a more accurate assessment and/or other result than a single modality of data alone, may have fewer false negatives and/or false positives than a single modality of data alone, or the like.

For example, an assessment module 104 may analyze image data such as magnetic resonance imaging (MRI) images, X-ray images, or the like of a brain of the user, volumetric data (e.g., volumetric measurements of a brain of the user), evaluation data for the user from a medical professional (e.g., a clinical diagnosis or other evaluation accounting for age, genetic indicators, or the like), and/or other modalities or types of data using machine learning to determine multiple predictions of likelihoods of the user getting a neurological disease, such as Alzheimer's disease or the like. An assessment module 104 may determine a single result based on the multiple predictions (e.g., a single and/or final clinical dementia rating (CDR), or the like).

An assessment module 104 may receive multiple types of data for a user and process the multiple types of data to determine if a person has a medical condition, such as a neurological disease. For example, an assessment module 104 may process the multiple types of data to compute a yes or no determination as to whether the person has the medical condition or to compute a score that indicates a probability or a likelihood that the person has the medical condition and/or a severity of the medical condition.

As used herein, a diagnosis or other result relates to any determination as to whether a person may have a medical condition or any determination as to a possible severity of the medical condition. A diagnosis or other result may include any form of an assessment, conclusion, opinion, or determination relating to a medical condition. In some instances, a diagnosis or other result may be incorrect, and a person diagnosed with a medical condition may not actually have the medical condition.

An assessment module 104 may receive the data for a user using any appropriate techniques. For example, a frontend assessment module 104*a* may be installed as an application or "app" on a hardware computing device 102 that uses a REST (representational state transfer) API call to transmit the multiple types of data over the internet, a mobile telephone network, or other data network 106 to a backend assessment module 104*b* installed on a backend server device 108. In another example, a medical professional may have a hardware computing device 102 that is used to record data for a person and transmit the data to an assessment module 104. In some embodiments, an assessment module 104 may be installed on a hardware computing device 102 such that it is not necessary to transmit the data over a data network 106.

An assessment module 104 may process multiple types of data with machine learning to perform a medical diagnosis. In processing the multiple types of data, features may be computed from the multiple types of data, and then the features may be processed by the machine learning. Any appropriate type of features may be used.

To train a machine learning model for diagnosing a medical condition, a corpus of training data may be collected. The training corpus may include examples of data where the diagnosis of the person is known. For example, it may be known that the person had no Alzheimer's disease, or a mild, moderate, or severe case of Alzheimer's disease. An assessment module 104 may use a training corpus that includes multiple types of data for training a machine learning model for diagnosing Alzheimer's disease and/or another neurological disease.

In one embodiment, the system 100 includes one or more hardware computing devices 102. The hardware computing devices 102 and/or the one or more backend server devices 108 (e.g., computing devices, information handling devices, or the like) may include one or more of a desktop computer, a laptop computer, a mobile device, a tablet computer, a smart phone, a set-top box, a gaming console, a smart TV, a smart watch, a fitness band, an optical head-mounted display (e.g., a virtual reality headset, smart glasses, or the like), an HDMI or other electronic display dongle, a personal digital assistant, and/or another computing device comprising a processor (e.g., a central processing unit (CPU), a processor core, a field programmable gate array (FPGA) or other programmable logic, an application specific integrated circuit (ASIC), a controller, a microcontroller, and/or another semiconductor integrated circuit device), a volatile memory, and/or a non-volatile storage medium. In certain embodiments, the hardware computing devices 102 are in communication with one or more backend server devices 108 via a data network 106, described below. The hardware computing devices 102, in a further embodiment, are capable of executing various programs, program code, applications, instructions, functions, or the like.

In various embodiments, an assessment module 104 may be embodied as hardware, software, or some combination of hardware and software. In one embodiment, an assessment module 104 may comprise executable program code stored on a non-transitory computer readable storage medium for execution on a processor of a hardware computing device 102; a backend server device 108; or the like. For example, an assessment module 104 may be embodied as executable program code executing on one or more of a hardware computing device 102; a backend server device 108; a combination of one or more of the foregoing; or the like. In such an embodiment, the various modules that perform the operations of an assessment module 104, as described below, may be located on a hardware computing device 102; a backend server device 108; a combination of the two; and/or the like.

In various embodiments, an assessment module 104 may be embodied as a hardware appliance that can be installed or deployed on a backend server device 108, on a user's hardware computing device 102 (e.g., a dongle, a protective case for a phone 102 or tablet 102 that includes one or more semiconductor integrated circuit devices within the case in communication with the phone 102 or tablet 102 wirelessly and/or over a data port such as USB or a proprietary communications port, or another peripheral device), or elsewhere on the data network 106 and/or collocated with a user's hardware computing device 102. In certain embodiments, an assessment module 104 may comprise a hardware device such as a secure hardware dongle or other hardware appliance device (e.g., a set-top box, a network appliance, or the like) that attaches to another hardware computing device 102, such as a laptop computer, a server, a tablet computer, a smart phone, or the like, either by a wired connection (e.g., a USB connection) or a wireless connection (e.g., Bluetooth®, Wi-Fi®, near-field communication (NFC), or the like); that attaches to an electronic display device (e.g., a television or monitor using an HDMI port, a DisplayPort port, a Mini DisplayPort port, VGA port, DVI port, or the like); that operates substantially independently on a data network 106; or the like. A hardware appliance of an assessment module 104 may comprise a power interface, a wired and/or wireless network interface, a graphical interface (e.g., a graphics card and/or GPU with one or more display ports) that outputs to a display device, and/or a semiconductor integrated circuit device as described below, configured to perform the functions described herein with regard to an assessment module 104.

An assessment module 104, in such an embodiment, may comprise a semiconductor integrated circuit device (e.g., one or more chips, die, or other discrete logic hardware), or the like, such as a field-programmable gate array (FPGA) or other programmable logic, firmware for an FPGA or other programmable logic, microcode for execution on a microcontroller, an application-specific integrated circuit (ASIC), a processor, a processor core, or the like. In one embodiment, an assessment module 104 may be mounted on a printed circuit board with one or more electrical lines or connections (e.g., to volatile memory, a non-volatile storage medium, a network interface, a peripheral device, a graphical/display interface. The hardware appliance may include one or more pins, pads, or other electrical connections configured to send and receive data (e.g., in communication with one or more electrical lines of a printed circuit board or the like), and one or more hardware circuits and/or other electrical circuits configured to perform various functions of an assessment module 104.

The semiconductor integrated circuit device or other hardware appliance of an assessment module 104, in certain embodiments, comprises and/or is communicatively coupled to one or more volatile memory media, which may include but is not limited to: random access memory (RAM), dynamic RAM (DRAM), cache, or the like. In one embodiment, the semiconductor integrated circuit device or other hardware appliance of an assessment module 104 comprises and/or is communicatively coupled to one or more non-volatile memory media, which may include but is not limited to: NAND flash memory, NOR flash memory, nano random access memory (nano RAM or NRAM), nanocrystal wire-based memory, silicon-oxide based sub-10 nanometer process memory, graphene memory, Silicon-Oxide-Nitride-Oxide-Silicon (SONOS), resistive RAM (RRAM), programmable metallization cell (PMC), conductive-bridging RAM (CBRAM), magneto-resistive RAM (MRAM), dynamic RAM (DRAM), phase change RAM (PRAM or PCM), magnetic storage media (e.g., hard disk, tape), optical storage media, or the like.

The data network 106, in one embodiment, includes a digital communication network that transmits digital communications. The data network 106 may include a wireless network, such as a wireless cellular network, a local wireless network, such as a Wi-Fi network, a Bluetooth® network, a near-field communication (NFC) network, an ad hoc network, and/or the like. The data network 106 may include a wide area network (WAN), a storage area network (SAN), a local area network (LAN), an optical fiber network, the internet, or other digital communication network. The data network 106 may include two or more networks. The data network 106 may include one or more servers, routers, switches, and/or other networking equipment. The data network 106 may also include one or more computer readable storage media, such as a hard disk drive, an optical drive, non-volatile memory, RAM, or the like.

The one or more backend server devices 108, in one embodiment, may include one or more network accessible computing systems such as one or more web servers hosting one or more web sites, an enterprise intranet system, an application server, an API server, an authentication server, or the like. A backend server device 108 may include one or more servers located remotely from the hardware computing devices 102. A backend server device 108 may include at least a portion of the assessment modules 104, may comprise hardware of an assessment module 104, may store executable program code of an assessment module 104 in one or more non-transitory computer readable storage media, and/or may otherwise perform one or more of the various operations of an assessment module 104 described herein for shared content tracking and attribution.

Figure 2:
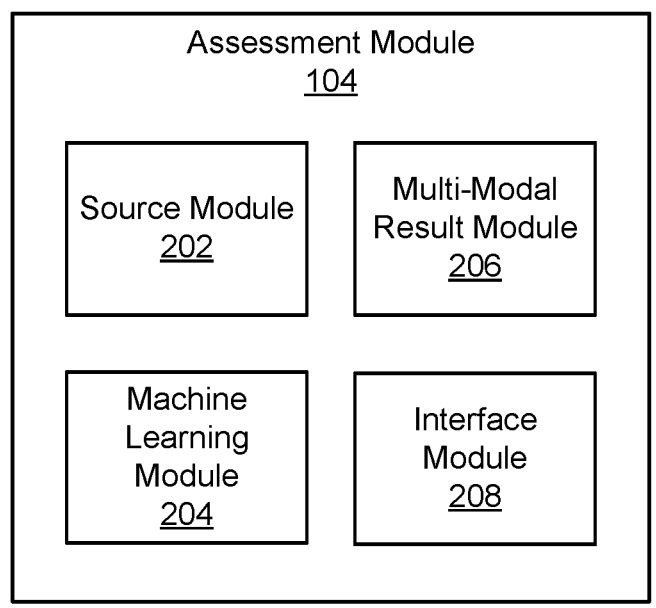
FIG. 2 is a schematic block diagram illustrating one embodiment of an assessment module.

FIG. 2 depicts one embodiment of an assessment module 104. The assessment module 104, in certain embodiments, may be substantially similar to one or more of a device assessment module 104a and/or a backend assessment module 104b, as described above with regard to FIG. 1. The assessment module 104, in the depicted embodiment, includes a source module 202, a machine learning module 204, a multi-modal result module 206, and an interface module 208.

In one embodiment, the source module 202 is configured to receive multiple types of data for a user. For example, in various embodiments, a source module 202 may receive image data of a brain of a user (e.g., MRI images, X-ray images, computerized tomography (CT) scan images, or the like), volumetric data (e.g., volumetric measurements, estimates, or the like) for a brain of a user, evaluation data for a user (e.g., clinical evaluation data from a doctor, nurse, and/or other medical professional, or the like), and/or other types of data relevant to a neurological disease or other medical condition.

In certain embodiments, a plurality of source modules 202 disposed on a plurality of different computing devices 102 may receive data for a plurality of different users. For example, a plurality of distributed source modules 202 may collect data samples for a medical trial, to train a machine learning model for diagnosing a medical condition, or the like.

The source module 202, in one embodiment, may store received multiple types of data on a computer readable storage medium of a computing device 102, 110, so that the machine learning module 204 may access and/or process the received multiple types of data to diagnose and/or assess a medical condition, train a machine learning model for diagnosing and/or assessing a medical condition, or the like; so that the interface module 208 may provide the received multiple types of data to one or more authorized users; and/or so that the received multiple types of data are otherwise accessible for use. In another embodiment, the source module 202 may provide received multiple types of data directly to the machine learning module 204 for diagnosing and/or assessing a medical condition (e.g., without otherwise storing the data, temporarily storing and/or caching the data, or the like). The source module 202 may store and/or organize received types of data in a database and/or other predefined data structure accessible by the machine learning module 204, the multi-modal result module 206, the interface module 208, or the like.

By storing multiple types of data for a user, in certain embodiments, the source module 202 may enable the machine learning module 204 and/or the multi-modal result module 206 to dynamically assess a medical condition for the user. For example, the source module 202 may store multiple types of data for a user on a hardware computing device 102, on a backend server device 108 in communication with a hardware computing device 102 over a data network 106, or the like, enabling the machine learning module 204 to determine an assessment of a medical.

In one embodiment, a machine learning module 204 is configured to analyze multiple types of data from a source module 202 using machine learning to determine multiple predictions of likelihoods of a user getting a neurological disease and/or other medical condition. For example, in some embodiments, a machine learning module 204 may use different machine learning models to process different types of data (e.g., a convolutional neural network comprising a residual neural network or the like to analyze image data of a brain of a user, a K nearest neighbor classifier to analyze volumetric data of a brain of a user, a random forest to analyze evaluation data of a user, or the like).

In one embodiment, the machine learning module 204 may determine multiple assessments or other predictions of a neurological disease or other medical condition for a user (e.g., indicating whether or not the user has the medical condition, a likelihood that the user will have the medical condition, an estimated severity of the medical condition, or the like), each based on a different type of data received for the user. The machine learning module 204, in certain embodiments, may determine binary predictions of whether a user is likely to get a neurological disease or other medical condition (e.g., yes or no, likely or unlikely, positive or negative, or the like).

In one embodiment a multi-modal result module 206 is configured to determine a single assessment and/or other result indicating a likelihood of a user getting a neurological disease or other medical condition based on multiple types of data from a source module 202 and/or multiple predictions from a machine learning module 204, or the like. For example, the multi-modal result module 206 may combine or otherwise process and/or analyze predictions for multiple types of data for a user, into a single assessment or other result indicating whether or not the user is likely to get a neurological disease or other medical condition.

The multi-modal result module 206 may use one or more rules to determine a single assessment and/or other result based on multiple predictions, multiple types of data, or the like. In one embodiment, the multi-modal result module 206 may use a conservative rule, and may be configured to determine that a user is likely to get a neurological disease or other medical condition in response to all of multiple predictions indicating the user is likely to get the neurological disease or other medical condition.

In a further embodiment, the multi-modal result module 206 may use a voting rule, and may be configured to determine that a user is likely to get a neurological disease or other medical condition in response to a majority of multiple predictions indicating the user is likely to get the neurological disease or other medical condition (e.g., at least two out of three, three out of four or five, four out of six or seven, five out of eight or nine, six out of ten or eleven, or the like).

In one embodiment, the multi-modal result module 206 may use an aggressive rule, and may be configured to determine that a user is likely to get a neurological disease or other medical condition in response to at least one of multiple predictions indicating that the user is likely to get the neurological disease or other medical condition (e.g., if any one type of data indicated that the user is likely to get the neurological disease, the multi-modal result module 206 determines that the user is likely to get the neurological disease).

In certain embodiments, the multi-modal result module 206 may use an override rule allowing a prediction based on one type of data to override one or more other predictions, types of data, or the like. For example, the multi-modal result module 206 may be configured to determine that a user is likely to get a neurological disease or other medical condition if a predefined type of data indicates that it is likely, if two predefined types of data indicate that it is likely, or the like. In one embodiment, the multi-modal result module 206 may be configured to determine that a user is likely to get a neurological disease or other medical condition in response to either an evaluation of the user by a medical professional indicating the user is likely to get the neurological disease or other medical condition (e.g., as an override type of data), or both image data of a brain of the user and volumetric data for the brain of the user indicating the user is likely to get the neurological disease or other medical condition (e.g., allowing two other types of data to counter the override type of data).

In some embodiments, instead of or in addition to one or more of the above rules, the multi-modal result module 206 may be configured to use a machine learning analysis to determine a single assessment or other result indicating a likelihood of the user getting a neurological disease or other medical condition (e.g., by processing the multiple types of data for the user from the source module 202 and/or the predictions from the machine learning module 204 as inputs into a machine learning model, such as a decision tree or other machine learning model, which may provide the single assessment or other result).

The interface module 208, in certain embodiments, is configured to execute on a hardware computing device 102 (e.g., of a user such as a medical professional evaluating a patient, a patient, of the like) and/or on a backend server device 108, or the like. In one embodiment, the interface module 208 may be configured to provide a user interface to a medical professional, a patient, and/or to another user. In a further embodiment, the interface module 208 is configured to provide an API to the source module 202, the machine learning module 204, the multi-modal result module 206, other interface modules 208, other assessment modules 104, hardware computing devices 102, backend server devices 108, or the like.

The interface module 208, in one embodiment, is configured to cooperate with the source module 202, the machine learning module 204, and/or the multi-modal result module 206. For example, the source module 202 may be configured to receive multiple types of data for a user through a user interface of the interface module 208 displayed on an electronic display screen of a hardware computing device 102 and to provide the multiple types of data to the machine learning module 204 using an API of the interface module 208, or the like. In a further example, the interface module 208 may be configured to receive a single assessment or other result indicating a likelihood of a user getting a neurological disease and/or another medical condition from the multi-modal result module 206 over an API of the interface module 208, and the interface module 208 may be configured to display the single result in a user interface on an electronic display screen of a hardware computing device 102.

In one embodiment, the interface module 208 provides one or more users with access to received types of data from the source module 202 (e.g., image data, volumetric data, evaluation data, or the like), to predictions and/or other results from the machine learning module 204 and/or the multi-modal result module 206, or the like. The interface module 208 may allow a user to access received types of data, predictions and/or other results, or the like from multiple locations (e.g., from a mobile app on a mobile computing device 102, from a web browser of a different computing device 102 accessing a web server of a backend server device 108, or the like).

In certain embodiments, the interface module 208 may enforce access control permissions (e.g., for privacy, for security, for HIPAA compliance, or the like) by authenticating users (e.g., with a username and password or other authentication credentials) and providing the users access to types of data, predictions or other results, or the like based on access control permissions associated with the user.

Figure 3:
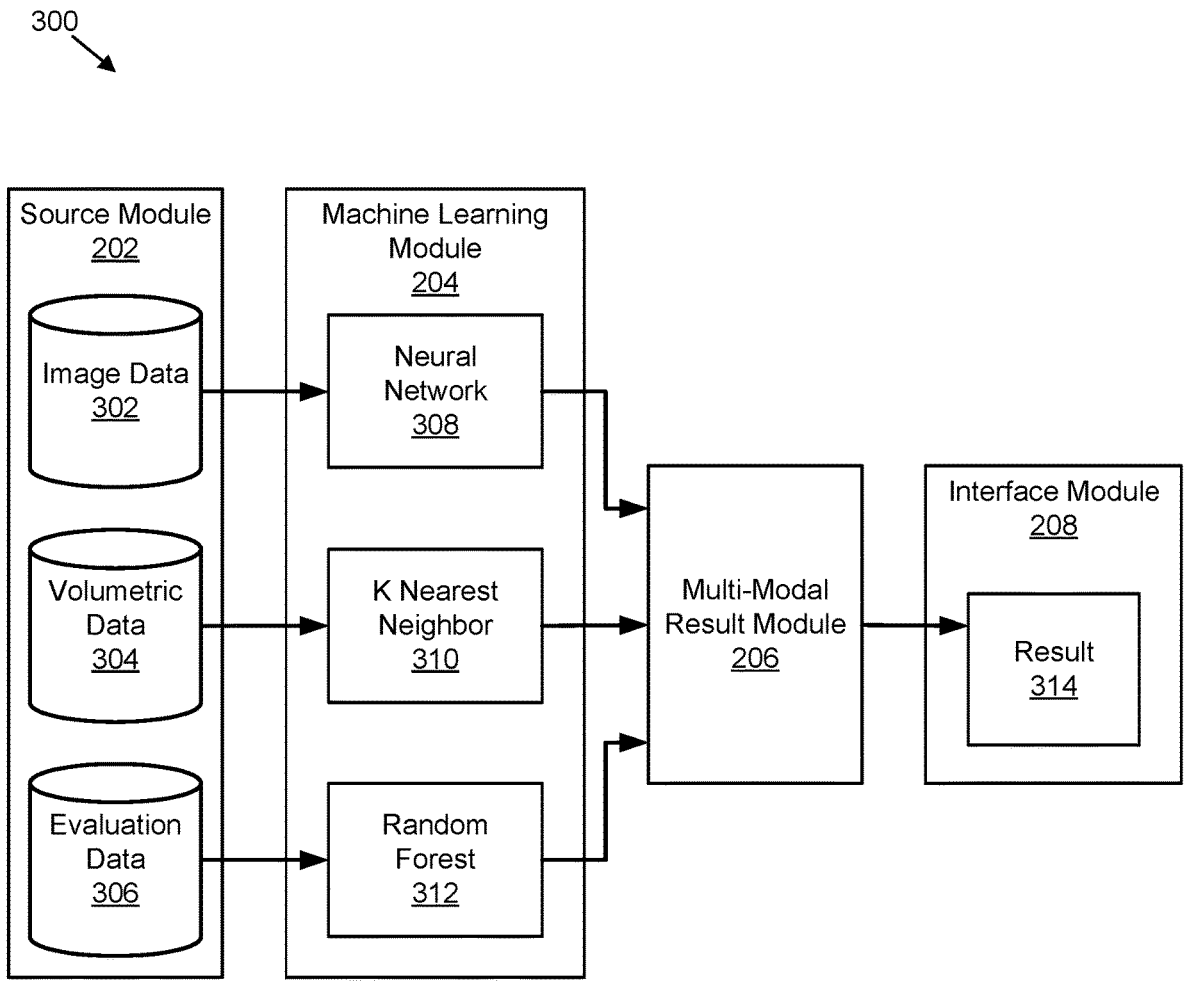
FIG. 3 is a schematic block diagram illustrating a further embodiment of a system for multi-modal machine learning medical assessment.

FIG. 3 depicts one embodiment of a system 300 for multi-modal machine learning medical assessment. In the depicted embodiment, the source module 202 receives image data 302, volumetric data 304, and evaluation data 306 and provides the received types of data 302, 304, 306 to the machine learning module 204. The machine learning module 204 analyzes the image data 302 using a neural network 308 (e.g., a convolutional neural network comprising a residual neural network, or the like) to determine a first prediction, analyzes the volumetric data 304 using a K nearest neighbor classifier 310 to determine a second prediction, and analyzes the evaluation data 306 using a random forest 312 to determine a third prediction.

In the depicted embodiment, the multi-modal result module 206 analyzes and/or combines the first, second, and third predictions of likelihoods of a user getting a neurological disease or other medical condition from the neural network 308, the K nearest neighbor classifier 310, and the random forest 312 to determine a single result 314 indicating a likelihood of the user getting the neurological disease or other medical condition (e.g., using a conservative rule, a voting rule, an aggressive rule, an override rule, a decision tree, or the like). The multi-modal result module 206 provides the result 314 to the interface module 208. The interface module 208 may display the result 314 to a user (e.g., a medical professional, a patient, and/or another user) on an electronic display screen of a hardware computing device 102, may provide the result 314 over an API in response to an API request, or the like.

Figure 4:
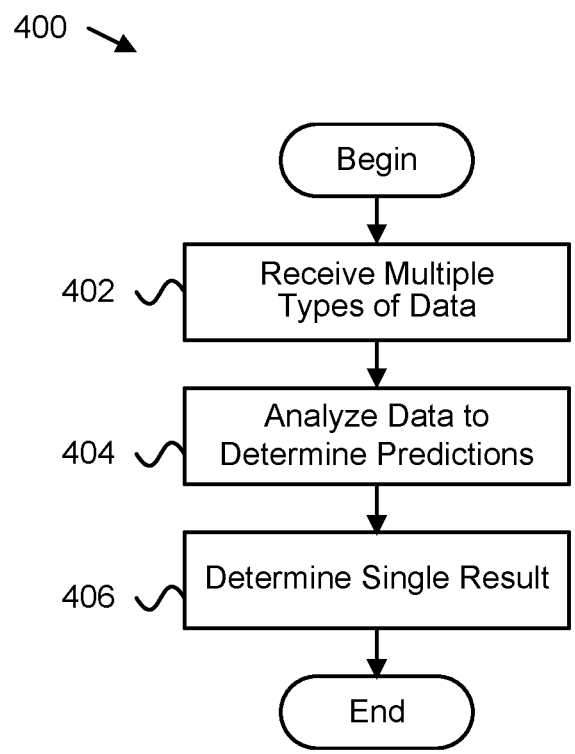
FIG. 4 is a schematic flowchart diagram illustrating one embodiment of a method for multi-modal machine learning medical assessment.

FIG. 4 depicts one embodiment of a method 400 for multi-modal machine learning medical assessment. The method 400 begins, and a source module 202 receives 402 multiple types of data for a user. A machine learning module 204 analyzes 404 the multiple types of data using machine learning to determine multiple predictions of likelihoods of the user getting a neurological disease or other medical condition. A multi-modal result module 206 determines 406 a single result indicating a likelihood of the user getting the neurological disease or other medical condition based on the multiple predictions and the method 400 ends.

Figure 5:
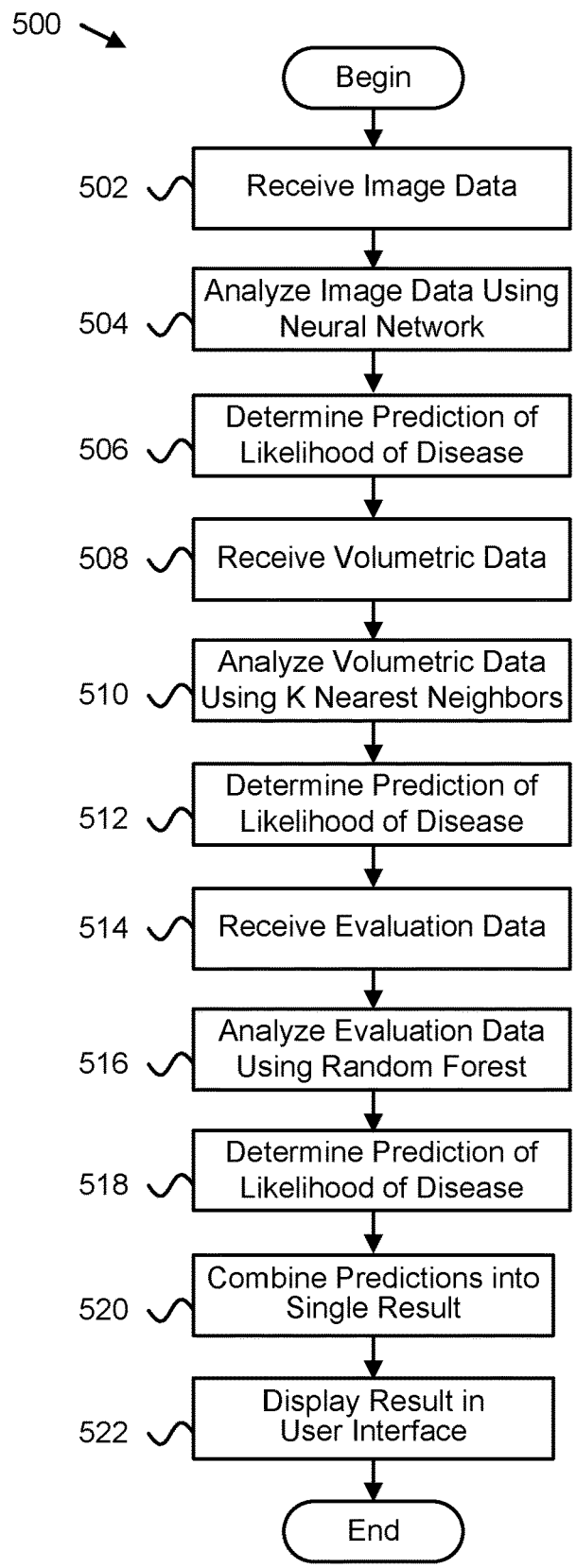
FIG. 5 is a schematic flowchart diagram illustrating a further embodiment of a method for multi-modal machine learning medical assessment.

FIG. 5 depicts one embodiment of a method 500 for multi-modal machine learning medical assessment. The method 500 begins, and a source module 202 receives 502 image data 302 of a brain of a user. A machine learning module 204 analyzes 504 the image data 302 using a neural network 308 and determines 506 a prediction of the likelihood of the user getting a neurological disease.

The source module 202 receives 508 volumetric data 304 for the brain of the user. The machine learning module 204 analyzes 510 the volumetric data 304 using a K nearest neighbor classifier 310 and determines 512 a prediction of the likelihood of the user getting the neurological disease. The source module 202 receives 514 an evaluation 306 of the user by a medical professional. The machine learning module 204 analyzes 516 the evaluation data 306 using a random forest 312 and determines 518 a prediction of the likelihood of the user getting the neurological disease.

A multi-modal result module 206 combines 520 the predictions 506, 512, 518 into a single result 314 indicating a likelihood of the user getting the neurological disease (e.g., using a conservative rule, a voting rule, an aggressive rule, an override rule, a decision tree, or the like). An interface module 208 displays 522 the single result 314 in a user interface on an electronic display screen of a hardware computing device 102 and the method 500 ends.

A means for receiving multiple types of data for a user, in various embodiments, may comprise an assessment module 104, a source module 202, an interface module 208, a hardware computing device 102, a hardware server device 108, a data network 106, an MRI device, an X-ray device, a CT scanner device, a camera or other optical sensor, a microphone or other audio sensor, another sensor device, a user interface, an API, a keyboard device, a network interface, a mobile application, a processor, an application specific integrated circuit (ASIC), a field programmable gate array (FPGA), programmable logic, other logic hardware, and/or other executable program code stored on a non-transitory computer readable storage medium. Other embodiments may comprise substantially similar or equivalent means for receiving multiple types of data for a user.

A means for analyzing multiple types of data using machine learning to determine multiple predictions of likelihoods of a user getting a neurological disease, in various embodiments, may comprise an assessment module 104, a machine learning module 204, a multi-modal result module 206, a hardware computing device 102, a hardware server device 108, a neural network 308, a K nearest neighbor classifier 310, a random forest 312, a mobile application, a processor, an application specific integrated circuit (ASIC), a field programmable gate array (FPGA), programmable logic, other logic hardware, and/or other executable program code stored on a non-transitory computer readable storage medium. Other embodiments may comprise substantially similar or equivalent means for analyzing multiple types of data using machine learning to determine multiple predictions of likelihoods of a user getting a neurological disease.

A means for determining a single result indicating a likelihood of a user getting a neurological disease based on multiple predictions, in various embodiments, may comprise an assessment module 104, a machine learning module 204, a multi-modal result module 206, a hardware computing device 102, a hardware server device 108, a decision tree, a mobile application, a processor, an application specific integrated circuit (ASIC), a field programmable gate array (FPGA), programmable logic, other logic hardware, and/or other executable program code stored on a non-transitory computer readable storage medium. Other embodiments may comprise substantially similar or equivalent means for determining a single result indicating a likelihood of a user getting a neurological disease based on multiple predictions.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus comprising:
a machine learning module configured to train different machine learning models using a corpus of training data comprising multiple different types of data associated with a neurological disease, the multiple different types of data comprising diagnosis data for patients with varying degrees of severity of the neurological disease;
a source module configured to receive multiple types of data for a user, the machine learning module configured to analyze the multiple types of data using the different machine learning models to process the multiple types of data to determine multiple predictions of likelihoods of the user getting a neurological disease; and
a multi-modal result module configured to determine a single result indicating a likelihood of the user getting the neurological disease based on the multiple predictions, the multiple predictions independently indicating whether the user is likely to get the neurological disease, the single result determined by applying one or more rules that each define an amount of the multiple predictions that indicate the user is likely to get the neurological disease that are needed for the single result to indicate that the user is likely to get the neurological disease, wherein a prediction based on a certain type of data has priority over a prediction based on a different type of data.

2. The apparatus of claim 1, wherein at least one of the multiple types of data comprises image data of a brain of the user.

3. The apparatus of claim 2, wherein the image data comprises magnetic resonance images of the brain of the user.

4. The apparatus of claim 2, wherein at least one of the multiple types of data comprises volumetric data for the brain of the user.

5. The apparatus of claim 4, wherein at least one of the multiple types of data comprises an evaluation of the user by a medical professional.

6. The apparatus of claim 5, wherein the machine learning module is configured to analyze the evaluation of the user by a medical professional using a random forest, to analyze the volumetric data of the brain of the user using K nearest neighbors, and to analyze the image data of the brain of the user using a convolutional neural network comprising a residual neural network.

7. The apparatus of claim 1, wherein the multi-modal result module is configured to determine the user is likely to get the neurological disease in response to one or more of the evaluation of the user by the medical professional indicating the user is likely to get the neurological disease, and both the image data of the brain of the user and the volumetric data for the brain of the user indicating the user is likely to get the neurological disease.

8. The apparatus of claim 1, wherein the multi-modal result module is configured to determine the user is likely to get the neurological disease in response to at least one of the multiple predictions indicating the user is likely to get the neurological disease.

9. The apparatus of claim 1, wherein the multi-modal result module is configured to determine the user is likely to get the neurological disease in response to a majority of the multiple predictions indicating the user is likely to get the neurological disease.

10. The apparatus of claim 1, wherein the multi-modal result module is configured to determine the user is likely to get the neurological disease in response to all of the multiple predictions indicating the user is likely to get the neurological disease.

11. The apparatus of claim 1, wherein the multi-modal result module is configured to determine the single result indicating the likelihood of the user getting the neurological disease by processing the multiple types of data for the user with machine learning comprising a decision tree.

12. The apparatus of claim 1, wherein the neurological disease comprises Alzheimer's disease.

13. The apparatus of claim 1, further comprising an interface module configured to execute on a computing device of a medical professional evaluating the user.

14. The apparatus of claim 13, wherein the source module is configured to receive the multiple types of data for the user through a user interface of the interface module displayed on an electronic display screen of the computing device and to provide the multiple types of data to the machine learning module using an application programming interface.

15. The apparatus of claim 14, wherein the interface module is configured to receive the single result indicating the likelihood of the user getting the neurological disease from the multi-modal result module over the application programming interface and to display the single result in the user interface on the electronic display screen of the computing device.

16. An apparatus comprising:
 means for training different machine learning models using a corpus of training data comprising multiple different types of data associated with a neurological disease, the multiple different types of data comprising diagnosis data for patients with varying degrees of severity of the neurological disease;
 means for receiving multiple types of data for a user;
 means for analyzing the multiple types of data using the different machine learning models to process the multiple types of data to determine multiple predictions of likelihoods of the user getting a neurological disease; and
 means for determining a single result indicating a likelihood of the user getting the neurological disease based on the multiple predictions, the multiple predictions independently indicating whether the user is likely to get the neurological disease, the single result determined by applying one or more rules that each define an amount of the multiple predictions that indicate the user is likely to get the neurological disease that are needed for the single result to indicate that the user is likely to get the neurological disease, wherein a prediction based on a certain type of data has priority over a prediction based on a different type of data.

17. The apparatus of claim 16, wherein the multiple types of data for the user comprise image data of a brain of the user, volumetric data for the brain of the user, and an evaluation of the user by a medical professional, and wherein the machine learning comprises a random forest to analyze the evaluation of the user by the medical professional, a K nearest neighbor classifier to analyze the volumetric data of the brain of the user, and a convolutional neural network comprising a residual neural network to analyze the image data of the brain.

18. A method comprising:
 training different machine learning models using a corpus of training data comprising multiple different types of data associated with a neurological disease, the multiple different types of data comprising diagnosis data for patients with varying degrees of severity of the neurological disease;
 receiving multiple types of data for a user;
 analyzing the multiple types of data using the different machine learning models to process the multiple types of data to determine multiple predictions of likelihoods of the user getting a neurological disease; and
 determining a single result indicating a likelihood of the user getting the neurological disease based on the multiple predictions, the multiple predictions independently indicating whether the user is likely to get the neurological disease, the single result determined by applying one or more rules that each define an amount of the multiple predictions that indicate the user is likely to get the neurological disease that are needed for the single result to indicate that the user is likely to get the neurological disease, wherein a prediction based on a certain type of data has priority over a prediction based on a different type of data.

19. The method of claim 18, wherein the multiple types of data for the user comprise image data of a brain of the user, volumetric data for the brain of the user, and an evaluation of the user by a medical professional.

20. The method of claim 19, wherein the machine learning comprises a random forest to analyze the evaluation of the user by the medical professional, a K nearest neighbor classifier to analyze the volumetric data of the brain of the user, and a convolutional neural network comprising a residual neural network to analyze the image data of the brain.

* * * * *